US010560529B2

(12) United States Patent
Jiang et al.

(10) Patent No.: US 10,560,529 B2
(45) Date of Patent: Feb. 11, 2020

(54) VEHICLE INFORMATION AND ENVIRONMENT MONITORING COMPOUND VEHICLE SYSTEM AND DATA PROCESSING AND TRANSMISSION METHOD THEREIN

(71) Applicant: NATIONAL TAIWAN UNIVERSITY, Taipei (TW)

(72) Inventors: Joe-Air Jiang, Taipei (TW); Chih-Hong Sun, Taipei (TW); Tzai-Hung Wen, Taipei (TW); Jehn-Yih Juang, Taipei (TW); Chien-Hao Wang, Taipei (TW); Zheng-Wei Ye, Taipei (TW); Chao-Liang Hsieh, Taipei (TW)

(73) Assignee: NATIONAL TAIWAN UNIVERSITY, New Taipei (TW)

( * ) Notice: Subject to any disclaimer, the term of this patent is extended or adjusted under 35 U.S.C. 154(b) by 98 days.

(21) Appl. No.: 15/809,930

(22) Filed: Nov. 10, 2017

(65) Prior Publication Data
US 2019/0075165 A1    Mar. 7, 2019

(30) Foreign Application Priority Data
Sep. 6, 2017    (TW) .............................. 106130485 A

(51) Int. Cl.
*H04L 29/08*    (2006.01)
*G01S 19/13*    (2010.01)
*G01N 33/00*    (2006.01)

(52) U.S. Cl.
CPC ............ *H04L 67/12* (2013.01); *G01N 33/004* (2013.01); *G01N 33/0031* (2013.01);
(Continued)

(58) Field of Classification Search
CPC ..................................................... H04L 67/12
See application file for complete search history.

(56) References Cited

U.S. PATENT DOCUMENTS 9,641,915 B2 *    5/2017    White, Jr. ................ H04Q 9/00
2015/0166072 A1    6/2015    Powers et al.
(Continued)

FOREIGN PATENT DOCUMENTS

CN    103342119 B    1/2016

OTHER PUBLICATIONS

Amr, "MQTT Protocol—How it Works", Jul. 2018 (Year: 2018).*
(Continued)

*Primary Examiner* — Ondrej C Vostal
(74) *Attorney, Agent, or Firm* — Intellectual Property Law Group LLP

(57) ABSTRACT

A vehicle information and environmental monitoring compound vehicle system is provided, including a sensor device used as a mobile sensor for collecting sensory data of roads, and the sensor device integrates various sensor modules and the second-generation on board computer diagnostic system serial port. The sensor device also integrates a long-distance low-power Internet of Things (LoRa) communication protocol, which can transmit data through the long-distance low-power Internet of Things gateway, and upload data to the cloud platform based on algorithm. The results of the analysis can establish a wide range of traffic congestion model through the detection information of traffic flow, and traffic density. The use of pixel-based measurement methods can quantify the urban road temperature, establish the urban heat island effect model, analyze the influence of temperature and humidity on the disease spread, establish the disease diffusion model, and display the sensor data in the graphical user interface.

11 Claims, 9 Drawing Sheets

(52) U.S. Cl.
CPC ..... *G01N 33/0037* (2013.01); *G01N 33/0039* (2013.01); *G01S 19/13* (2013.01); *H04L 67/10* (2013.01)

(56) References Cited

U.S. PATENT DOCUMENTS

| | | | |
|---|---|---|---|
| 2016/0028780 A1* | 1/2016 | Verzano | H04W 4/70 709/204 |
| 2016/0357522 A1* | 12/2016 | Wee | G06F 16/29 |
| 2016/0359664 A1* | 12/2016 | Malegaonkar | G06F 8/34 |
| 2017/0006141 A1* | 1/2017 | Bhadra | H04W 4/70 |
| 2017/0272842 A1* | 9/2017 | Touma | G08C 17/02 |
| 2017/0310767 A1* | 10/2017 | Flynn, IV | H04W 4/70 |
| 2017/0351241 A1* | 12/2017 | Bowers | G05B 19/406 |
| 2017/0364612 A1* | 12/2017 | Broodney | G06F 17/5009 |
| 2018/0054490 A1* | 2/2018 | Wadhwa | G06F 9/45558 |
| 2018/0062959 A1* | 3/2018 | Justin | H04W 4/70 |
| 2018/0165978 A1* | 6/2018 | Wood | G05B 19/0423 |
| 2018/0213378 A1* | 7/2018 | Brown | H04W 4/70 |
| 2018/0285306 A1* | 10/2018 | Essmann | G06F 13/4208 |
| 2019/0173755 A1* | 6/2019 | Jadhav | H04L 12/4625 |

OTHER PUBLICATIONS

Bo, "Introducing Android phones to the Internet of Things via WebSphere MQ Telemetry Transport (MQTT)", 2011 (Year: 2011).*
Chen et al., "Performance Evaluation of IoT Protocols under a Constrained Wireless Access Network", 2016 (Year: 2016).*
Cohn et al., "Oasis MQTT Version 3.1.1 Oasis Standard", 2014 (Year: 2014).*
Grgic et al., "A Web-Base IoT Solution for Monitoring Data Using MQTT Protocol", 2016 (Year: 2016).*
IBM, "MQTT V3.1 Protocol Specification", Copyright 1999-2010 (Year: 1999).*
Pearce, "The Magic of MQTT", 2019 (Year: 2019).*
Standord-Clark et al., "MQTT for Sensor Networks (MQTT-SN) Protocol Specification Version 1.2", 2013 (Year: 2013).*

* cited by examiner

VEHICLE INFORMATION AND ENVIRONMENT MONITORING COMPOUND VEHICLE SYSTEM AND DATA PROCESSING AND TRANSMISSION METHOD THEREIN

CROSS-REFERENCE TO RELATED APPLICATION

This application claims benefit of Taiwan, R.O.C. patent application no. 106130485 filed Sep. 6, 2017, the disclosure of which is hereby incorporated by reference in its entirety for all purposes.

BACKGROUND OF THE INVENTION

1. Field of the Invention

The present disclosure relates to a vehicle monitoring system and a method thereof, and more particularly to a vehicle information and environment monitoring compound vehicle system and a data processing and transmission method therein.

2. Description of Related Art

Smart city is an important economic strategic blueprint for a country's economic transformation and upgrade. Many countries have been in the vanguard of the technological advance and initiated smart city development programs, such as the smart grids in the US and the intelligent energy management in Amsterdam. In Taiwan, the Taipei City government has established "Taipei Smart City PMO (the Project Management Office)" to promote projects and be a bridge of the government and the public. These projects promote the development of smart city. Our environment has become worse because of air pollution. The air pollutants, including PM2.5/10, carbon monoxide, nitrogen dioxide, ozone, and sulfur dioxide, are harmful to the public. To deal with serious air pollution problems, the Environmental Protection Administration, Executive Yuan, R.O.C. (Taiwan) has established a system to monitor gas all over Taiwan and shows the results on a map in real time. The map is a graphical user interface which allows people to obtain information regarding gas air pollution conditions and the amount of fouling. The government agency has also established an air quality index (AQI) which determines air quality conditions by using six levels, including good, moderate, unhealthy for sensitive groups, unhealthy, very unhealthy, and hazardous. However, the gas observation station is far from each other, which a problem for air pollution is monitoring. In this study, a vehicle monitoring system (VMS) equipped with several sensors, such as sensors that measure PM2.5, CO, $NO_2$, $O_3$ and GPS, second-generation on board computer diagnostic system, and temperature/humidity is proposed. With the VMS, the air quality parameters could be measured while driving a car on the street and a wide range of areas would be monitored. The communication of VMS is based on the LoRa technique, which is a transmission protocol controlled by LoRa Alliance™. LoRaWAN™ is a low power wide area network (LPWAN) specification which could operate things in a regional, national or global network. The advantages of using the LoRa technique are low power consumption and long transmission distance. These advantages are important to the proposed VMS. On the other hand, the LoRaWAN also possesses some key elements of Internet of Things (IoT), such as localization services, mobility networking, and secure communication. The LoRaWAN specification provides an easy operating way between things without the requirement of complicated installations, and it makes users feel free to engage in IoT application. The IoT refers to the connection of devices to the Internet. Cars, house appliances, and even environmental monitors can all be connected via the IoT. When the Internet of Things increases in the future, more devices will have connection with each other. With the LoRa Alliance™, the VMS could connect to other vehicles, devices, and be a part of IoT. Finally, the VMS can also play a significant role of Smart City in the future.

With the advancement in technology and the increasing development in cities, many urban problems such as traffic congestion, air pollution, urban heat-island effect, and disease diffusion may arise. For the sake of overcoming those problems, the present disclosure employs an application of combining a car with IoT to develop an Internet of Vehicles system based on IoT for Smart City. In addition, the existing vehicles are equipped with GPS and provide interior parameters, and lack a combination of GPS and vehicle interior parameters with gas sensors, thus leaving room for improvement in the drawback.

SUMMARY OF THE INVENTION

According to one exemplary embodiment of the present disclosure, a vehicle information and environmental monitoring compound vehicle system is provided, including a sensor device (i.e. the aforementioned vehicle system, which can be a V-box in practice), a long-distance low-power Internet of Things gateway, a cloud platform, and a graphical user interface. The sensor device is equipped in a car and used as a mobile sensor for collecting a first sense data, in which the first sense data at least includes GPS positioning information, vehicle information, air quality information and weather information; the sensor device includes a processor configured to process the first sense data to produce a data packet. The long-distance low-power Internet of Things gateway (i.e. LoRa gateway) is communicated with the sensor device and adjacent to the sensor device, and configured to receive and transmit the data packet. The cloud platform is communicated with the long-distance low-power Internet of Things gateway to receive and transmit the data packet. The graphical user interface is communicated with the cloud platform to receive and display second sense data. In addition, the sensor device further includes a transmission module including a long-distance low-power Internet of Things transmission module which has the wireless network transmission technology of a long-distance low-power Internet of Things (LoRa) communication protocol, making the sensor device to transmit the data packet to the long-distance low-power Internet of Things gateway. The long-distance low-power Internet of Things gateway transmits the data packet to the cloud platform. After decoding the data packet, the cloud platform produces the second sense data, and the second sense data is displayed in the graphical user interface through Message Queuing Telemetry Transport (MQTT), thereby allowing citizens or government bureaus and departments to conveniently go online to conduct search for information.

According to another exemplary embodiment of the present disclosure, a data processing and transmission method using the information and environmental monitoring compound vehicle system mentioned above is provided, at least including: initializing the sensor device; initializing the GPS module; initializing the second-generation on board computer diagnostic system module; the GPS module obtaining the GPS positioning information; the second-generation on board computer diagnostic system module obtaining the vehicle information; the plurality of gas sensors sensing the air pollution information and the weather information; compressing and coding the first sense data to generate the data packet; transmitting the data packet by the long-distance low-power Internet of Things transmission module; transmitting the data packet to the cloud platform by the long-distance low-power Internet of Things gateway; determining whether the cloud platform receives the data packet; when the cloud platform receives the data packet, decoding the data packet to generate the second sense data and displaying the second sense data in the graphical user interface; or retransmitting the data packet by the long-distance low-power Internet of Things gateway if the cloud platform does not receive the data packet.

The vehicle information and environment monitoring compound vehicle system of the present disclosure is not only capable of instantly monitoring the vehicle information, gas information, and environment parameters, but also monitoring the vehicle speed, engine speed, coolant temperature, and engine load, as well as $CO_2$, CO, $O_3$, total suspended particulate (TSP) and PM2.5/10 of gases.

The vehicle information and environment monitoring compound vehicle system of the present disclosure is combined with IoT and employs a car as a mobile sensor node to collect data, and a wireless sensor of IoT technology of is introduced into the present system. After the mobile sensor node collected and gathered the sense data, the data can be transmitted to the adjacent gateway through the wireless network transmission technology, and after the gateway summarized the information, the sense data is uploaded to the cloud database, and the uploaded sense data is displayed in the graphical user interface 400 (GUI).

The vehicle information and environment monitoring compound vehicle system of the present disclosure is to dispose the sensor on a micro controller, and the micro controller can be connected to multiple sensors and display the test results in the computer GUI through the Universal Asynchronous Receiver/Transmitter (UART). The initial operations are all processed by the chip of the micro controller.

The vehicle information and environment monitoring compound vehicle system of the present disclosure is equipped with the automatic storing function to compensate the potential data loss when the data is in the process of transmitting through the wireless sensing network. In addition, the automatic storing function can also synchronously store the sense data such as the temperature/relative humidity, gas sensing parameters, three-axis accelerometer parameters, GPS position, and vehicle information in a temporary space, thereby promoting the percentage of data retention.

A vehicle information and environment monitoring compound vehicle system and a data processing and transmission method using the vehicle information and environment monitoring compound vehicle system are provided in the present disclosure. Conventional vehicles are equipped with GPS and vehicle information functions without integrating gas sensors and environment parameters. The present disclosure, however, integrates vehicle, environment and gas sensors and uses a vehicle as a mobile sensor node to collect data, thereby intensively collecting gas parameters with respect to sensory data of roads, streets and so on. By analyzing the huge data, the gas model can be established more effectively and efficiently. In addition, the established model can provide predictions and observations to the government to make corresponding decisions.

In order to further understand the techniques, means and effects of the present disclosure, the following detailed descriptions and appended drawings are hereby referred to, such that, and through which, the purposes, features and aspects of the present disclosure can be thoroughly and concretely appreciated; however, the appended drawings are merely provided for reference and illustration, without any intention to be used for limiting the present disclosure.

BRIEF DESCRIPTION OF THE DRAWINGS

The accompanying drawings are included to provide a further understanding of the present disclosure, and are incorporated in and constitute a part of this specification. The drawings illustrate exemplary embodiments of the present disclosure and, together with the description, serve to explain the principles of the present disclosure.

DETAILED DESCRIPTION OF EXEMPLARY EMBODIMENTS

Figure 1:
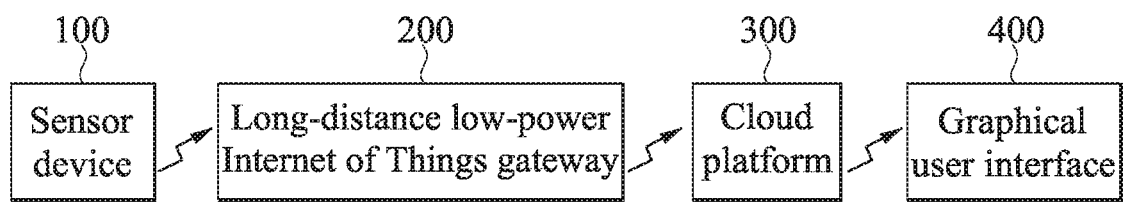
FIG. 1 is an architecture diagram of a vehicle information and environmental monitoring compound vehicle system of the present disclosure.

Reference will now be made in detail to the exemplary embodiments of the present disclosure, examples of which are illustrated in the accompanying drawings. Wherever possible, the same reference numbers are used in the drawings and the description to refer to the same or like parts.

Figure 2:
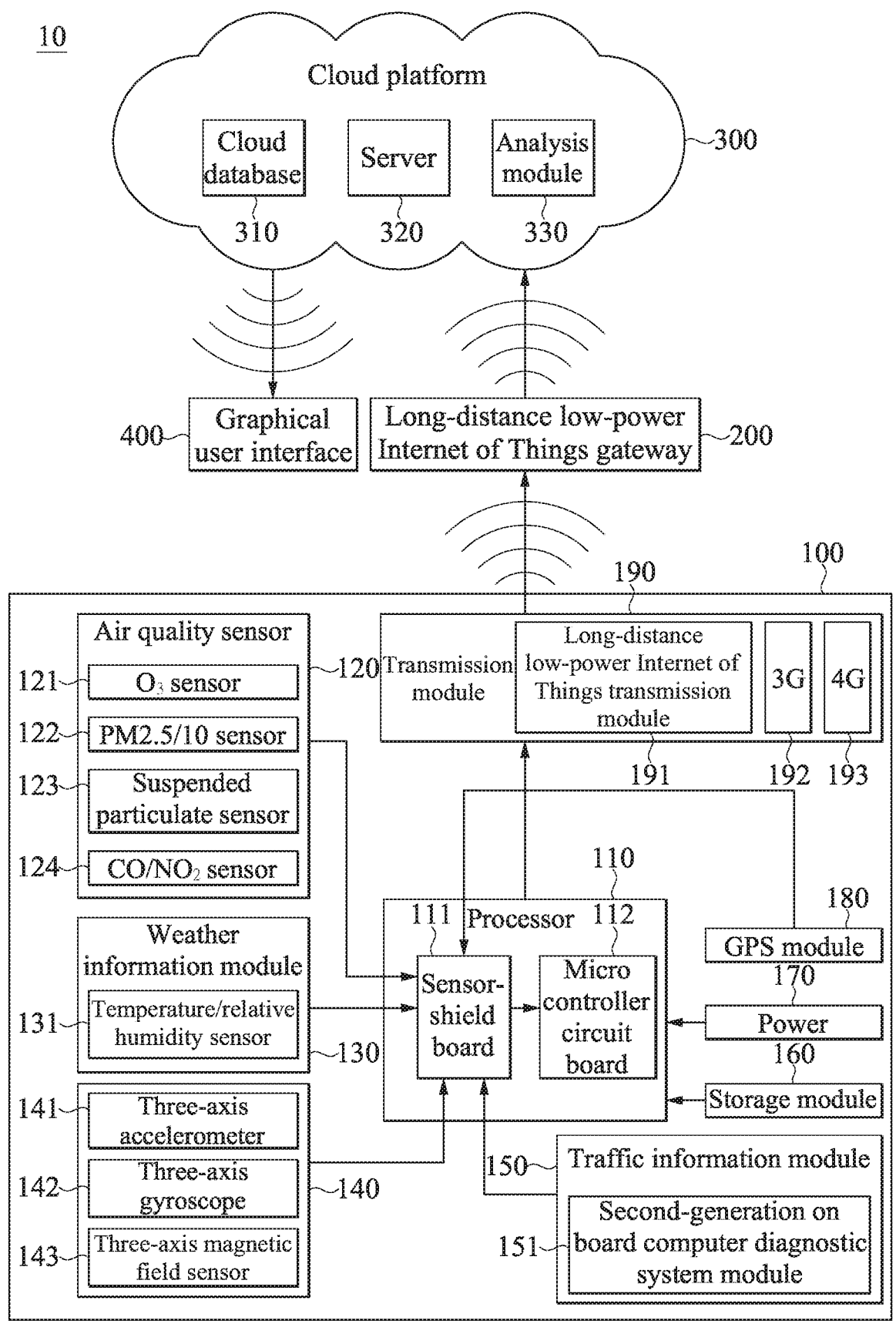
FIG. 2 is a functional block diagram of the vehicle information and environmental monitoring compound vehicle system according to one embodiment of the present disclosure.

FIG. 1 is an architecture diagram of a vehicle information and environmental monitoring compound vehicle system 1 of the present disclosure. The system of the present disclosure not only receives traffic information instantly but also monitors air conditions on the road. The present disclosure includes a sensor device 100, a long-distance low-power Internet of Things gateway 200, a cloud platform 300, and a graphical user interface 400. The sensor device 100 is disposed in a vehicle and served as a mobile sensor. The long-distance low-power Internet of Things gateway 200 is communicated with the sensor device 100, in which the long-distance low-power Internet of Things is LoRa. The cloud platform 300 is communicated with the long-distance low-power Internet of Things gateway 200. The graphical user interface 400 is communicated with the cloud platform 300 and designed for users to browse the traffic information. With the vehicle information and environmental monitoring compound vehicle system 1, users can better understand the real-time vehicle and air quality conditions on the street. And the big data collected by the vehicle information and environmental monitoring compound vehicle system 10 can help government agencies make corresponding strategic decisions Reference is made to FIG. 2, which is a functional block diagram of the vehicle information and environmental monitoring compound vehicle system 10 according to one embodiment of the present disclosure. The vehicle information and environmental monitoring compound vehicle system 10 includes the sensor device 100, a processor 110, an air quality sensor 120, a weather information module 130, a posture sensing module 140, a traffic information module 150, a storage module 160, a power 170, a Global Positioning System (GPS) module 180, and a transmission module 190. The sensor device 100 is disposed in a vehicle and served as a mobile sensor for collecting first sense data, in which the first sense data includes GPS positioning information, vehicle information, air quality information and weather information. The sensor device 100 includes the processor 110, the long-distance low-power Internet of Things gateway 200, the cloud platform 300, and the graphical user interface 400. The processor 110 is configured to process the first sense data to produce a data packet. The long-distance low-power Internet of Things (LoRa) gateway 200 is communicated with the sensor device 100 and adjacent to the sensor device 100, and is configured to receive and transmit the data packet. The cloud platform 300 is communicated with the long-distance low-power Internet of Things gateway 200 to receive and display the data packet. The graphical user interface 400 is communicated with the cloud platform 300 to receive and display second sense data. The sensor device 100 further includes the transmission module 190, in which the transmission module 190 includes a long-distance low-power Internet of Things transmission module 191 which has the wireless network transmission technology of a long-distance low-power Internet of Things (LoRa) communication protocol, enabling the sensor device 100 to transmit the data packet to the long-distance low-power Internet of Things gateway 200. The long-distance low-power Internet of Things gateway 200 can transmit the data packet to the cloud platform 300. After decoding the data packet, the cloud platform 300 can produce the second sense data, and the second sense data can be displayed in the graphical user interface 400 through the Message Queuing Telemetry Transport (MQTT), thereby allowing citizens or government bureaus and departments to conveniently go online to conduct search for information.

The processor 110 in the present embodiment includes a micro controller circuit board 112 and a sensor-shield board (SSB) 111, in which the sensor-shield board 111 is connected to the micro controller circuit board 112.

The sensor device 100 in the present embodiment further includes a plurality of gas sensors connected to the sensor device 110. The gas sensors include the air quality sensor 120 and the weather information module 130. The traffic information module 150 is connected to the processor 110, and includes a second-generation on board computer diagnostic system module 151 configured to produce the vehicle information. The GPS module 180 is connected to the processor 110 and configured to position the vehicle location and produce the GPS positioning information. The posture sensing module 140 is connected to the processor 110, and includes a three-axis accelerometer 141, a three-axis gyroscope 142 and a three-axis magnetic field sensor 143. The air quality sensor 120, the weather information module 130, the traffic information module 150, and the GPS module 180 are respectively connected to the micro controller circuit board 112 through the sensor-shield board 111.

In the present embodiment, the air quality sensor 120 includes an $O_3$ sensor 121, a PM2.5 sensor 122, a suspended particulate sensor 123 and a $CO/NO_2$ sensor 124, which are configured to sense the air quality outside a vehicle and produce the air quality information. The weather information module 130 includes a temperature/relative humidity sensor 131 configured to sense the surroundings outside the vehicle to produce the weather information.

In the present embodiment, the sensor device 100 includes the storage module 160 connected to the processor 110 and configured to automatically store the data packet wirelessly transmitted in the vehicle information and environmental monitoring compound vehicle system 10. In practice, the storage module 160 is a SD module.

In the present embodiment, the micro controller circuit board 112 is disposed with a chip (not shown). In practice, the chip can be a single chip which can operate the first sense data collected by the sensor device 100 and display the operation result in a computer graphical user interface.

In the present embodiment, the sensor device 100 can be a mobile sensor, and the functions and specifications of the main hardware components of the sensor device 100 designed for the disclosed system are disclosed as follows. The sensor device 100 includes a vehicle shield processor (VSP) which is composed of the micro controller circuit board 112 (an Arduino mega 2560) and the sensor-shield board (SSB) 111. In practice, the micro controller circuit board 112 (an Arduino mega 2560) is a microcontroller board based on the ATmega2560 which is a high performance and low power consumption Atmel® AVR® 8-Bit Microcontroller. Because a large number of sensors are employed by the vehicle information and environmental monitoring compound vehicle system 10, a microcontroller with enough digital, analog and UART pins is selected. The Arduino mega 2560 has 54 digital input/output pins, 16 analog inputs, 4 UARTs, a 16 MHz clock speed oscillator, a USB port, a power jack, an ICSP header, and a reset button. And it can be easily connected with a computer. The sensor-shield board 111 is connected to the micro controller circuit board 112 (an Arduino mega 2560). And other sensors, such as the temperature/relative humidity sensor, the GPS module 180, the vehicle information module 150, and the air quality sensor 120 can be connected to the micro controller circuit board 112 through the sensor-shield board 111 without pins.

In the present embodiment, the transmission module 190 in the disclosed vehicle information and environmental monitoring compound vehicle system 10 is the GIoT Module_GL6509. The transmission module 130 uses the Low Power Wide Area Network (LPWAN) specification. The transmission module 190 has two bands of 868 and 915 MHz. It can be adapted to different applications. And it supports AT commands, so users can operate it easily. The interface of the transmission module 190 includes GPIO, UART, and $I^2C$, making it easy to connect with the VSP. The long-distance low-power Internet of Things transmission module 191 has the advantages of low power consumption, user friendly, and wide area networking, the LoRa module is appropriate to achieve the goals of this study. In another embodiment, the transmission module 190 can transmit data through 3G/4G communication protocol.

In the present embodiment, the weather information module 130 is a SHT11 module, and ambient temperature and humidity is measured by the weather information module 130. The weather information module 130 is the temperature/relative humidity sensor 131 from the Sensirion family. The weather information module 130 integrates sensor components and signal processing chips on a tiny foot print and provides a fully calibrated digital output. A unique capacitive sensor element is used for measuring relative humidity while temperature is measured by a band-gap sensor. The temperature/relative humidity sensor 131 is seamlessly coupled to a 14 bit analog to digital converter and a serial interface circuit. This results in superior signal quality, a fast response time and insensitivity to external disturbances. The 2-wire serial interface and internal voltage regulation allows for easy and fast system integration. The tiny size and low power consumption is the reason why we choose it as the temperature and humidity sensor. The sensing ranges of the temperature/relative humidity sensor 131 in temperature (T) and relative humidity (% RH) are from −40 to 123.8° C. and from 0 to 100% RH, respectively, and the measurement resolutions in temperature and relative humidity are 0.01° C. and 0.05% RH @ 25° C., respectively. The measurement accuracy in temperature and relative humidity of SHT11 is ±0.4° C. and ±3.0% RH.

In the present embodiment, the vehicle information module 150 includes information regarding the engine, intake/exhaust, speed/time, driver, and electric systems from the car. By means of the second-generation on board computer diagnostic system module 151, such as the Freematics OBD-II (On board diagnostics II) I$^2$C Adapter for Arduino, the vehicle information could be easily obtained by connecting the car with the VSP through the I$^2$C protocol. The adapter is also equipped with the ELM327 chip which supports AT commands to obtain the corresponding information. Different protocols, such as CAN 500 Kbps/29 bit, CAN 250 Kbps/29 bit, KWP 2000 Fast, and KWP 2000 5 Kpbs, are integrated with the adapter, so it can be installed on different cars.

In the present embodiment, the air quality sensor 120 used in the vehicle information and environmental monitoring compound vehicle system 10 includes the $O_3$ sensor 121 such as MQ-131 ($O_3$), the $CO/NO_2$ sensor 124 such as MICS-4514 ($CO/NO_2$), and the suspended particulate sensor 123 such as GP2Y10 (TSP), and the PM2.5/10 sensor 122 such as OneAir A4 (PM). The $O_3$ sensor 121 has advantages of fast responses, high sensitivity, stable and long life, simplified drive circuits, and a wide detection range, and is suitable for monitoring $O_3$. The detection range is 10 ppb-2 ppm. The $CO/NO_2$ sensor 124 is a robust MEMS sensor responsible for the detection of the pollution from automobile exhausts. The detection range for carbon monoxide is from 1 to 1000 ppm and for nitrogen dioxide is from 0.05 to 10 ppm. The suspended particulate sensor 123 is a dust sensor operated by an optical sensing system. The suspended particulate sensor 123 detects the reflected light of dust in the air, and is effective to detect very fine particles and can be used as an air quality monitor. The PM2.5/10 sensor 122, which can be a PM 0.3/2.5/10 sensor, operates following the principle of a laser scattering theory. In the air, the suspended particulate in the air will be scattered by laser irradiation. The scattered light is collected at a specific angle to obtain the information of the scattering intensity over time. The measuring range is 0-6000 μg/m$^3$ and the operating temperature is at 10 to 50° C. With these sensors, gas which causes air pollution can be monitored in real time.

In the present embodiment, the GPS module 180 is equipped with a single chip such as a blox NEO-7M chip. The horizontal localization accuracy is 2.5 m and the sensitivity is 161 dBm when racking and navigation are performed. The GPS module 180 takes 28 seconds for the module to initiate a cold/warm start.

Figure 3:
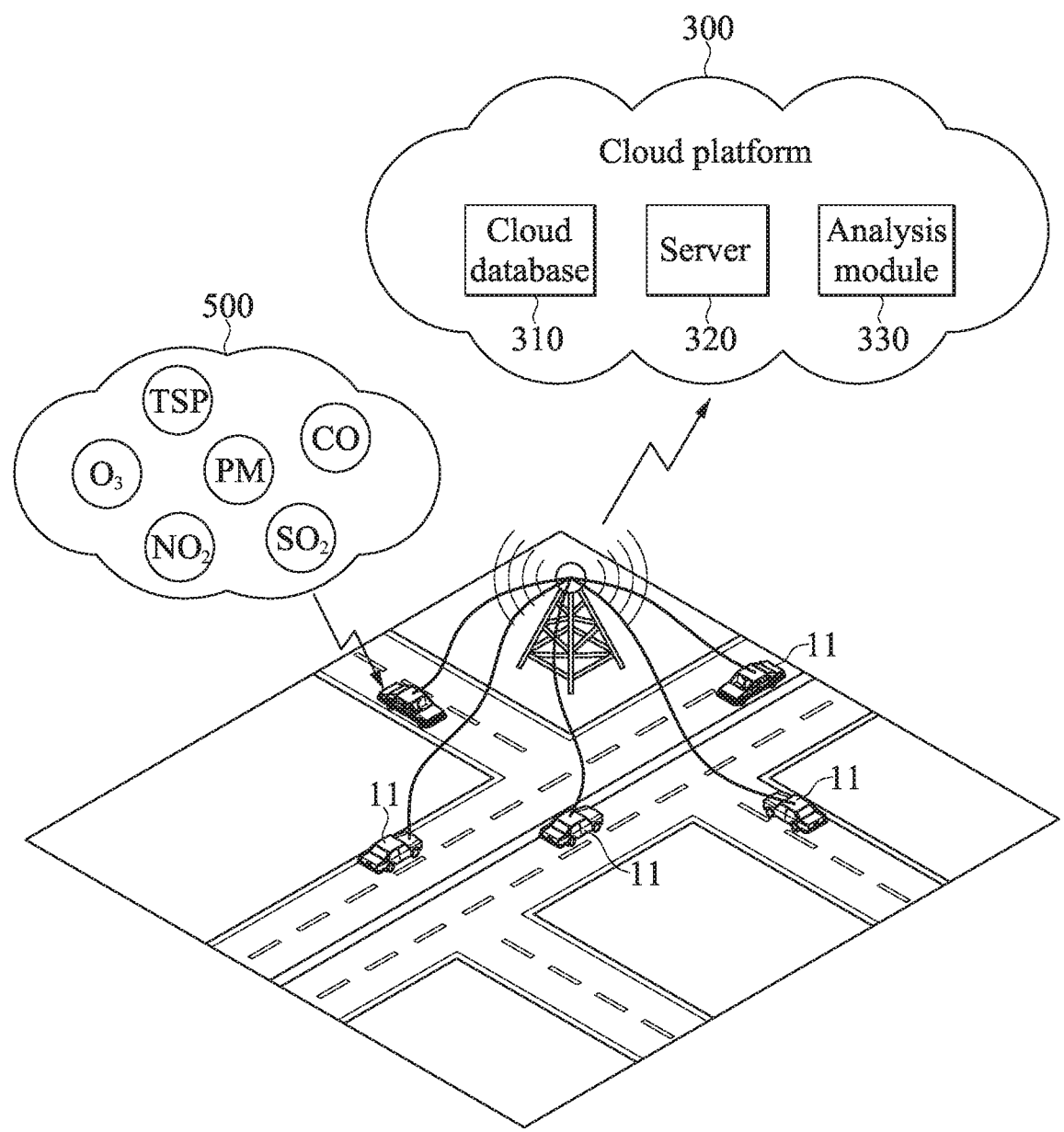
FIG. 3 is a schematic diagram of environment monitoring according to one embodiment of the present disclosure.

FIG. 3 is a schematic diagram of environment monitoring according to one embodiment of the present disclosure. In the present disclosure, a car 11 is equipped with the sensor device 100, so that the vehicle can collect the sense data of air 500 quality while moving. The sensor device 100 can detect the sense data with respect to that the air 500 contains $NO_2$, CO, $O_3$, TSP, PM2.5/10 an other gas concentrations, and then transmit the sense data to the cloud platform 300 through the long-distance low-power Internet of Things gateway 200.

Figure 4:
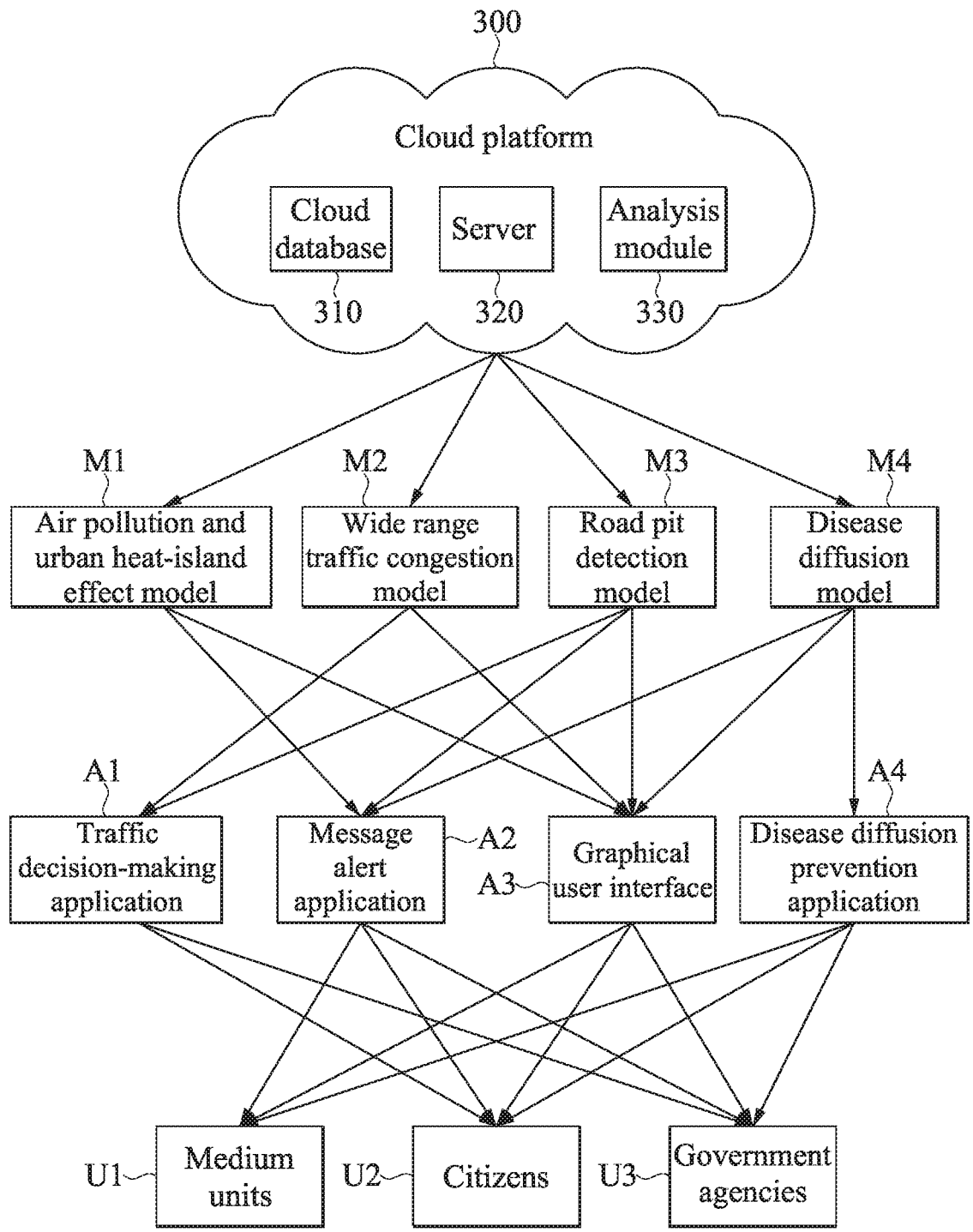
FIG. 4 is a functional block diagram of a cloud platform according to one embodiment of the present disclosure.

FIG. 4 is a functional block diagram of the cloud platform 300 according to one embodiment of the present disclosure. The cloud platform 300 includes a cloud database 310, a server 320, and an analysis module 330. The data packet transmitted to the cloud platform 300 through the long-distance low-power Internet of Things gateway 200 can be stored in the cloud database 310. The analysis module 330 reads the data packet stored in the cloud database 310 through the server 320, and analyzes the data packet to establish a plurality of models which at least includes an air pollution and urban heat-island effect module M1, a wide range traffic congestion model M2, a road pit detection model M3, and a disease diffusion model M4, in which the air pollution and urban heat-island effect model M1 can be adapted to a message alert application A2, the wide range traffic congestion model M2 can be adapted to a traffic decision-making application A1, and the road pit detection model M3 can be adapted to the message alert application A2 and a disease diffusion prevention application A4. In addition, the plurality of modules M1-M4 can all display the data in a graphical user interface A3, and the plurality of applications A1-A4 can all provide the data to medium units U1, citizens U2 and government agencies U3 for inquiry.

Figure 5:
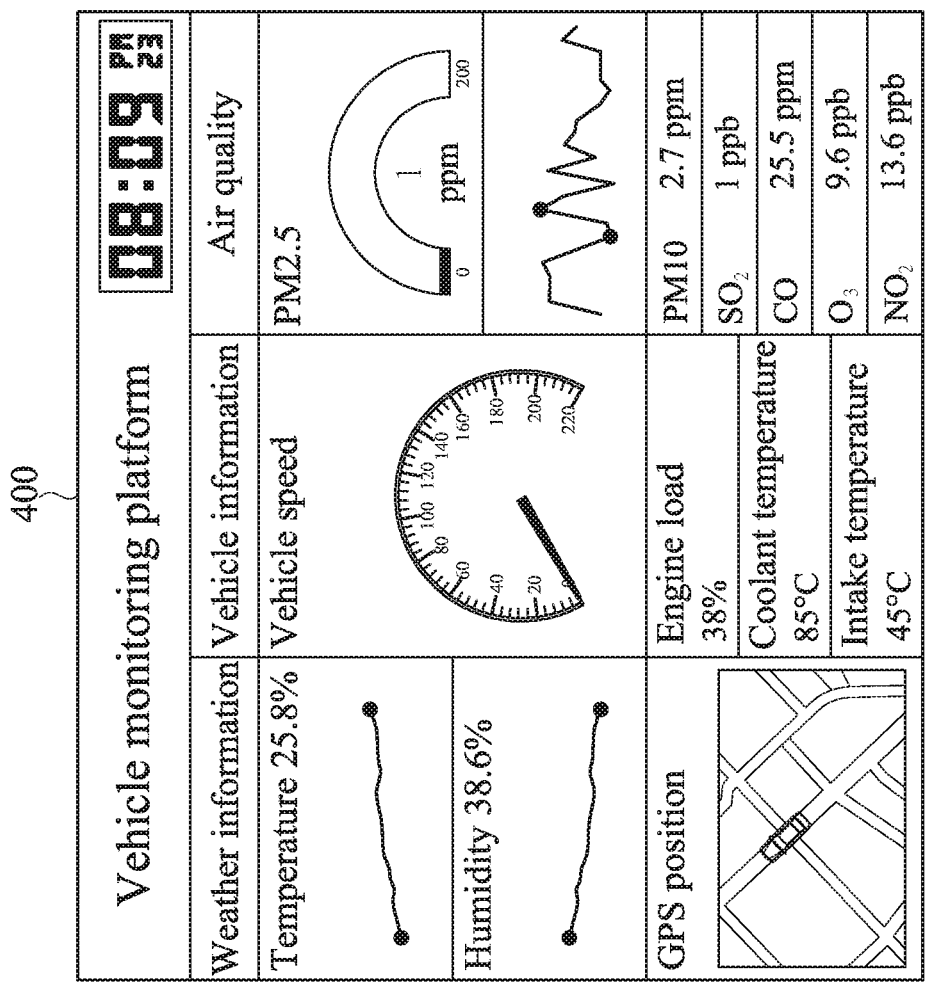
FIG. 5 is a schematic diagram of a graphical user interface according to one embodiment of the present disclosure.

FIG. 5 is a schematic diagram of the graphical user interface 400 according to one embodiment of the present disclosure. The second sense data received by the graphical user interface 400 includes the weather information, the GPS positioning information, the vehicle information and the air quality information gathered by the first sense data.

The data obtained by the sensor device 100 is transmitted to the long-distance low-power Internet of Things gateway 200 through the long-distance low-power Internet of Things transmission module 191. In another embodiment, the long-distance low-power Internet of Things gateway 200 is installed at each district in Taipei City by the Taipei City Government. The long-distance low-power Internet of Things gateway 200 has some limitations. For example, only one packet can be sent per minute, and each packet only contains data up to 11 bytes. The data transmission in this study is therefore arranged accordingly. After a packet is sent to the long-distance low-power Internet of Things gateway 200, the long-distance low-power Internet of Things gateway 200 will upload the data to a back-end database. The monitoring information will exhibit on a platform such as an IBM Bluemix platform through the MQTT protocol. The interface is divided into four major parts: weather information, GPS localization, vehicle information, and air quality. The graphical user interface 400 allows users to easily obtain air quality information from the website.

Figure 6:
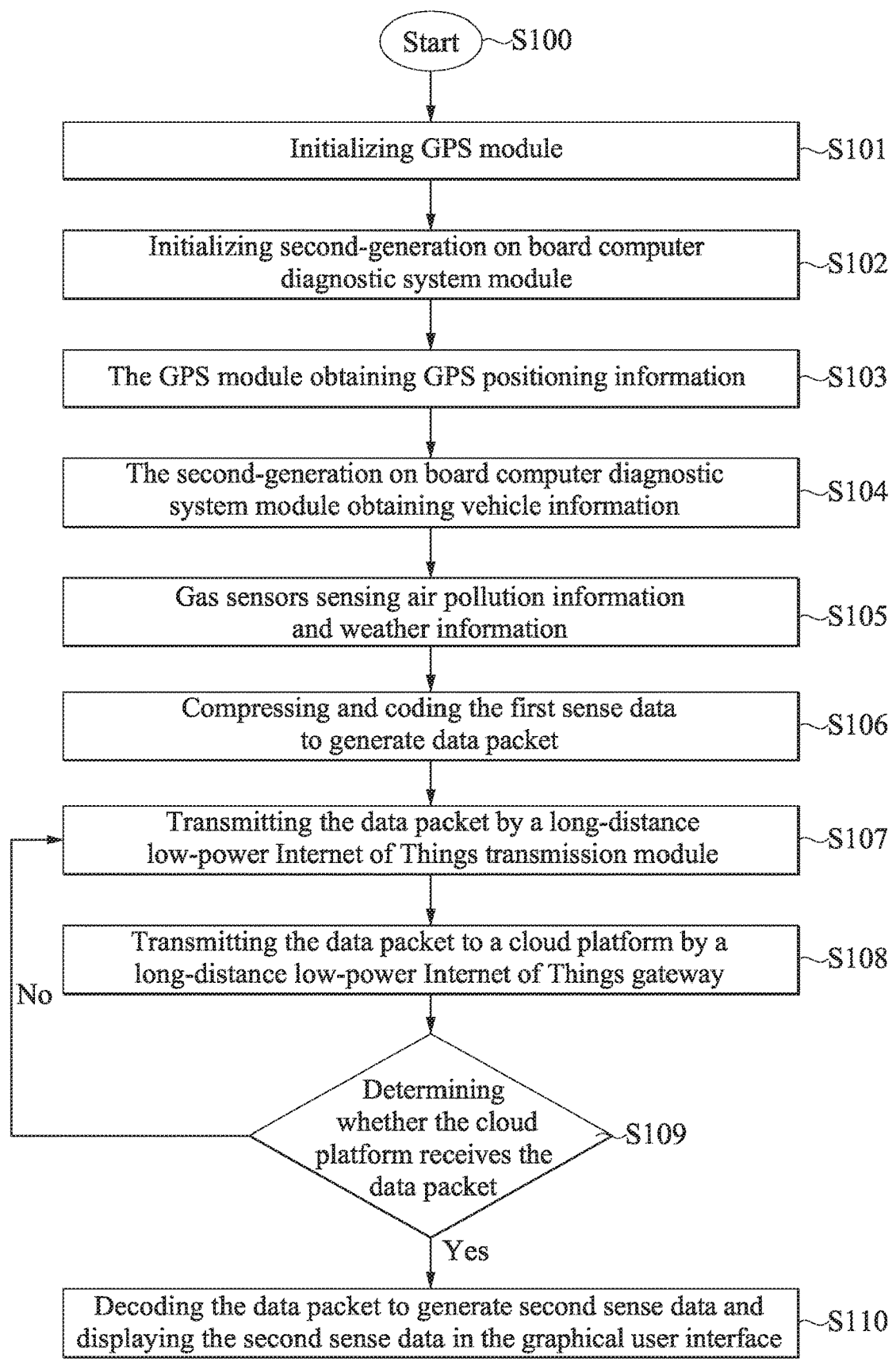
FIG. 6 is a flow chart of a data processing and transmission method using the information and environmental monitoring compound vehicle system according to one embodiment of the present disclosure.

FIG. 6 is a flow chart of data processing and transmission method using the information and environmental monitoring compound vehicle system according to one embodiment of the present disclosure. The data processing and transmission method using the information and environmental monitoring compound vehicle system 10 includes the following steps: start (S100); initializing the GPS module (S101); initializing the second-generation on board computer diagnostic system module (S102); the GPS module obtaining the GPS positioning information (S103); the second-generation on board computer diagnostic system module obtaining the vehicle information (S104); the plurality of gas sensors sensing the air quality information and the weather information (S105); compressing and coding the first sense data to generate the data packet (S106); transmitting the data packet by the long-distance low-power Internet of Things transmission module (S107); transmitting the data packet to the cloud platform by the long-distance low-power Internet of Things gateway (S108); determining whether the cloud platform receives the data packet (S109); if the cloud platform receives the data packet, decoding the data packet to generate second sense data and displaying the second sense data in the graphical user interface (S110); if the cloud platform does not receive the data packet, retransmitting the data packet through S107.

The operation procedure of the vehicle information and environmental monitoring compound vehicle system 10 is disclosed as follows. In the beginning, the sensor device 100 waits for a few seconds to start up the GPS module 180. The GPS module 180 provides the results of localization after warming up. After having the localization information, the vehicle information and environmental monitoring compound vehicle system 10 connects to a car, and it takes 3-5 seconds for the connection. Different AT commands will send to the MCU on the car to request the vehicle information module 150 to measure different parameters including car speed, rotational speed, intake temperature, and coolant temperature. And then the air quality sensor 120 measures different parameters, such as $O_3$, CO, $NO_2$, TSP, and PM. The raw monitoring data are transformed into a bit type to form a data packet. The transmission type of the long-distance low-power Internet of Things transmission module 191 is hex, so it is necessary to transform the data packet from binary bit to hex. Then, the data packet is sent to the long-distance low-power Internet of Things gateway 200 by the long-distance low-power Internet of Things transmission module 191. When the data packet is successfully sent to the cloud database 300, the monitoring information will be displayed in the graphical user interface 400 for users to browse. The location information of the car will update every 70 seconds.

Figure 7:
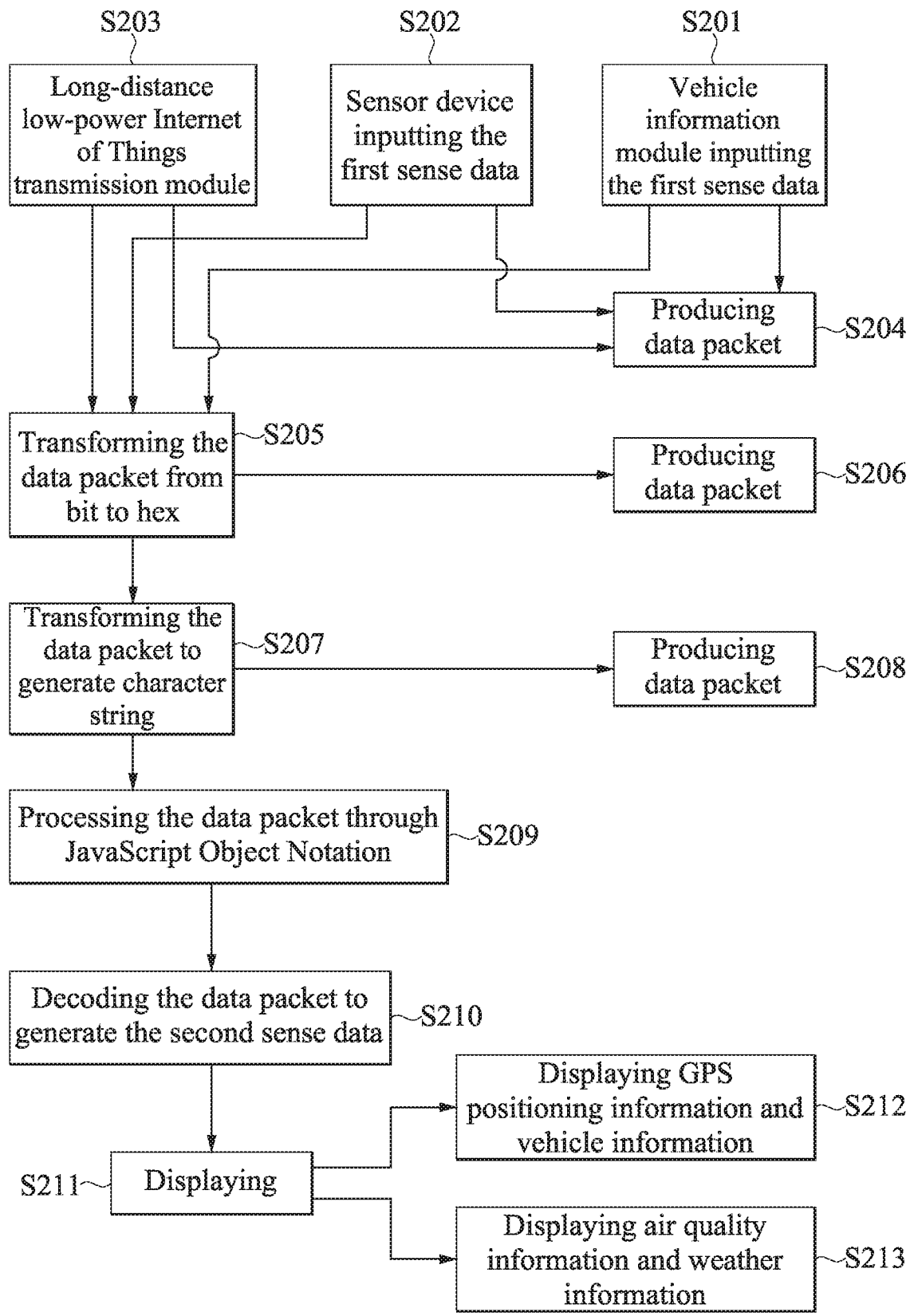
FIG. 7 is a flow chart of a back-end program according to one embodiment of the present disclosure.

FIG. 7 is a flow chart of a back-end program according to one embodiment of the present disclosure. After receiving the data packet S204 produced by S201, S202 and S203, the cloud platform 300 further decodes the data packet to generate second sense data, and displays the second sense data in the graphical user interface 400. The aforementioned method includes the following steps: the cloud platform 300 transforming the data packet from binary bit to hex (S205), including the step of producing the data packet (S206); the cloud platform 300 transforming the data packet to generate character string (S207), including the step of producing the data packet (S208); the cloud platform 300 processing the data packet through JavaScript Object Notation (S209); the cloud platform 300 decoding the data packet to generate second sense data (S210); and displaying the second sense data in the graphical user interface through the Message Queuing Telemetry Transport (MQTT) (S211), in which S211 further includes displaying the GPS positioning information and the vehicle information S211, and displaying the air quality information and the weather information S212.

After decoding the data packet to generate the second sense data, the cloud platform 300 further analyzes the second sense data, which includes: establishing a plurality of modules which at least includes an air pollution and urban heat-island effect model M1, a wide range traffic congestion model M2, and a disease diffusion model M4, and the plurality of models are at least adapted to a traffic decision-making application A1, a message alert application A2, and a disease diffusion prevention application A4.

Figure 8:
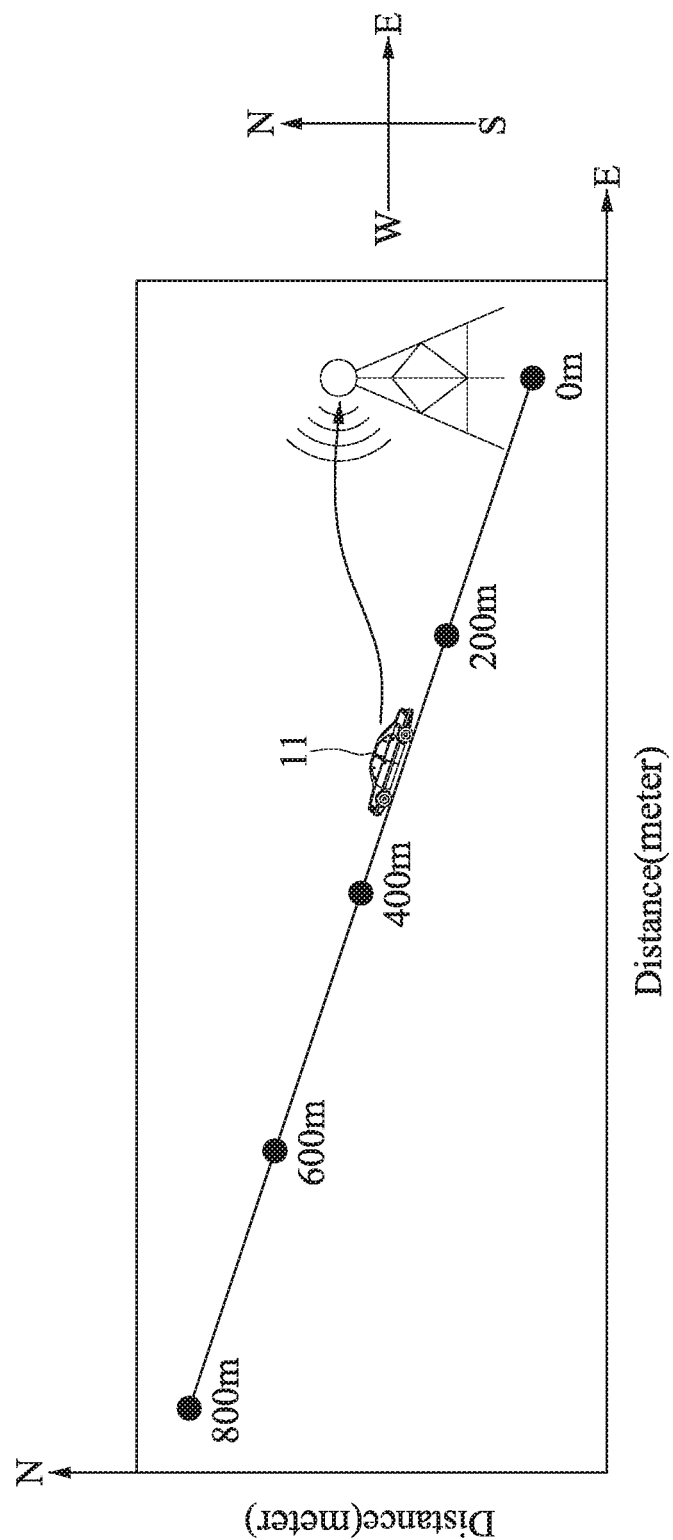
FIG. 8 is a route map illustrating a test of long distance transmission and low power consumption according to one embodiment of the present disclosure.
Figure 9:
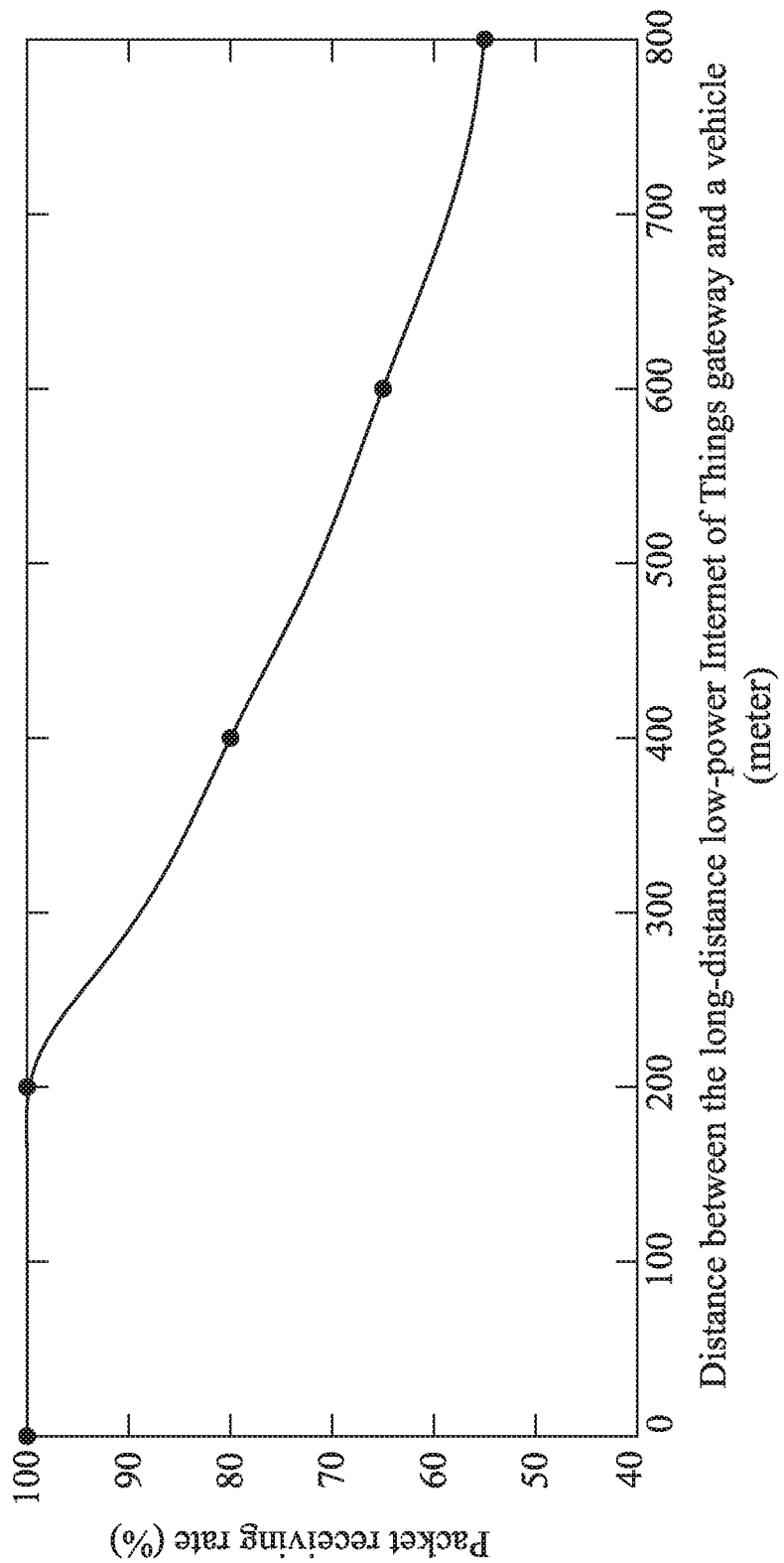
FIG. 9 is a schematic diagram illustrating a test result of the long distance transmission and low power consumption according to another embodiment of the present disclosure.

FIG. 8 is a route map illustrating a test of long distance transmission and low power consumption according to one embodiment of the present disclosure. To evaluate the performance of the long-distance low-power Internet of Things transmission module 191 used by the vehicle information and environmental monitoring compound vehicle system 10, the car 11 was driven around the Da'an District office in Taipei and tested the packet receiving rate. The long-distance low-power Internet of Things gateway 200 was located close to the Da'an District office. The tested distance between the car 11 and the long-distance low-power Internet of Things gateway 200 was 0 m (at the Da'an District office), 200 m, 400 m, 600 m, and 800 m. The driving route is shown in FIG. 9. And at each location, the test lasted for 10 minutes. The formula of calculating the packet received rate is shown as follows.

$$R = \frac{P_{received}}{P_{sent}} \times 100\%$$

$P_{received}$ is the amount of data packets in the database, $P_{sent}$ is the amount of data packet sent from the sensor node, and the R is the packet receiving rate (%) of the long-distance low-power Internet of Things gateway 200.

FIG. 9 is a schematic diagram illustrating a test result of the long distance transmission and low power consumption according to another embodiment of the present disclosure. The vertical axis is a packet receiving rate (%), the lateral axis is a distance between the long-distance low-power Internet of Things gateway 200 and the sensor device 100. A 100% packet receiving rate is found when the distance between the long-distance low-power Internet of Things gateway 200 and the sensor device 100 is 0 m (at Da'an District office) and 200 m. And the packet receiving rate declines when the sensor device 100 is away from the Da'an District office. It is noted that only a few long-distance low-power Internet of Things gateways 200 are deployed in Taipei City. The monitoring coverage will greatly increase, if the number of the deployed long-distance low-power Internet of Things gateway 200 increases.

In summary, the sensor device 100 of the present disclosure can be used as a mobile sense node to collect sensory data of roads, and can integrate various sensor modules with the second-generation on board computer diagnostic system module serial port. In addition, the sensor device 100 can also integrate the long-distance low-power Internet of Things (LoRa) communication protocol and transmit data through the long-distance low-power Internet of Things gateway, and upload data to the cloud platform 300 based on algorithm. The results of the analysis can be expected to establish a wide range of traffic congestion model through the detection information of traffic flow, traffic and traffic density. The use of pixel-based measurement methods can quantify the urban road temperature, establish the urban heat island effect model, analyze the influence of temperature and humidity on the disease spread, establish the disease diffusion model, and display the sensor data in the graphical user interface 400. And all of the data would be gathered and presented in the graphical user interface from users to browse the information. Besides, the data could also be provided to the government to make corresponding decisions.

The descriptions illustrated supra set forth simply the preferred embodiments of the present disclosure; however, the characteristics of the present disclosure are by no means restricted thereto. All changes, alterations, or modifications conveniently considered by those skilled in the art are deemed to be encompassed within the scope of the present disclosure delineated by the following claims.

What is claimed is:

1. A vehicle information and environmental monitoring compound vehicle system, comprising:
    a sensor device equipped in a car and used as a mobile sensor for collecting a first sense data, wherein the first sense data at least includes GPS positioning information, vehicle information, air quality information and weather information; the sensor device includes a processor configured to process the first sense data to produce a data packet;
    a long-distance low-power Internet of Things gateway communicating with the sensor device and adjacent to the sensor device, and configured to receive and transmit the data packet;
    a cloud platform communicating with the long-distance low-power Internet of Things gateway to receive and transmit the data packet; and
    a graphical user interface communicating with the cloud platform to receive and display second sense data;
    wherein, the sensor device further comprises a transmission module including a long-distance low-power Internet of Things transmission module which has the wireless network transmission technology of a long-distance low-power Internet of Things (LoRa) communication protocol, making the sensor device to transmit the data packet to the long-distance low-power Internet of Things gateway; the long-distance low-power Internet of Things gateway transmits the data packet to the cloud platform; after decoding the data packet, the cloud platform produces the second sense data, and the second sense data is displayed in the graphical user interface through Message Queuing Telemetry Transport (MQTT) protocol, allowing citizens, government bureaus and departments a convenience of conducting information searching online.

2. The vehicle information and environmental monitoring compound vehicle system according to claim 1, wherein the processor comprises a micro controller circuit board and a sensor-shield board, the sensor-shield board is connected to the micro controller circuit board, and the sensor device further comprises:
    a plurality of gas sensors connected to the processor and including an air quality sensor and a weather information module;
    a vehicle information module connected to the processor and including a second-generation on board computer diagnostic system module configured to produce the vehicle information;
    a GPS module connected to the processor for positioning a car position and producing the GPS positioning information; and
    a posture sensing module connected to the processor and including a three-axis accelerometer, a three-axis gyroscope, and a three-axis magnetic field sensor;
    wherein, the air quality sensor, the weather information module, the traffic information module, and the GPS module are respectively connected to the micro controller circuit board through the sensor-shield board.

3. The vehicle information and environmental monitoring compound vehicle system according to claim 2, wherein the air quality sensor comprises an O3 sensor, a PM2.5 sensor, a suspended particulate sensor and a CO/NO2 sensor, which are configured to sense the air quality outside a vehicle and produce the air quality information;
    wherein, the weather module includes a temperature/relative humidity sensor configured to sense the surroundings outside the vehicle to produce the weather information.

4. The vehicle information and environmental monitoring compound vehicle system according to claim 1, wherein the sensor device comprises a storage module connected to the processor, for automatically storing the data packet wirelessly transmitted in the vehicle information and environmental monitoring compound vehicle system.

5. The vehicle information and environmental monitoring compound vehicle system according to claim 3, wherein the micro control circuit board is disposed with a chip used to operate the first sense data collected by the sensor device and display the operation result in a computer graphical user interface.

6. The vehicle information and environmental monitoring compound vehicle system according to claim 3, wherein the graphical user interface receives the second sense information, and displays the weather information, the GPS positioning information, the vehicle information and the air quality information gathered by the first sense data.

7. The vehicle information and environmental monitoring compound vehicle system according to claim 3, wherein the cloud platform comprises an analysis module configured to analyze the data packet to establish a plurality of models which at least includes a wide range of traffic congestion model, a disease diffusion model, and an air pollution and urban heat island effect model, wherein, the plurality of models are at least adapted to a traffic decision-making application, a message alert application, and a disease diffusion prevention application.

8. A data processing and transmission method, comprising:
    initializing a GPS module connected to a processor of a sensor device that is equipped in a car and used as a mobile sensor for collecting a first sense data including GPS positioning information generated by the GPS module, vehicle information, air quality information and weather information, wherein the processor of the sensor device is configured to process the first sense data to produce a data packet;
    initializing a second-generation on board computer diagnostic system module that is configured to produce the vehicle information;
    the GPS module obtaining the GPS positioning information;
    the second-generation on board computer diagnostic system module obtaining the vehicle information;
    a plurality of gas sensors sensing the air quality information and the weather information;

compressing and coding the first sense data to generate the data packet;

transmitting the data packet by a long-distance low-power Internet of Things transmission module included in a transmission module of the sensor device for communicating with the sensor device and adjacent to the sensor device and for receiving and transmitting the data packet; wherein the long-distance low-power Internet of Things transmission module implements a wireless network transmission technology of a long-distance low-power Internet of Things (LoRa) communication protocol, and the transmission module makes the sensor device to transmit the data packet to the long-distance low-power Internet of Things gateway; further, the long-distance low-power Internet of Things gateway transmits the data packet to a cloud platform that communicates with the long-distance low-power Internet of Things gateway; after decoding the data packet, the cloud platform produces a second sense data, and the second sense data is displayed in a graphical user interface communicating with the cloud platform through Message Queuing Telemetry Transport (MQTT) protocol, and allowing citizens, government bureaus and departments a convenience of conducting information searching online;

transmitting the data packet to the cloud platform by the long-distance low-power Internet of Things gateway;

determining whether the cloud platform receives the data packet;

when the cloud platform receives the data packet, the cloud platform decoding the data packet to generate the second sense data and displaying the second sense data in the graphical user interface; and retransmitting the data packet by the long-distance low-power Internet of Things gateway if the cloud platform does not receive the data packet.

9. The data processing and transmission method according to claim 8, wherein: the step of when the cloud platform receives the data packet, the cloud platform decoding the data packet to generate the second sense data and displaying the second sense data in the graphical user interface further comprises:

the cloud platform transforming the data packet from binary bit to hex;

the cloud platform transforming the data packet to generate character string;

the cloud platform processing the data packet through JavaScript Object Notation;

the cloud platform decoding the data packet to generate the second sense data, and displaying the second sense data in the graphical user interface through the Message Queuing Telemetry Transport.

10. The data processing and transmission method according to claim 8, wherein after the step of decoding the data packet to generate the second sense data, the method further comprises:

analyzing the sense information; and establishing a plurality of models which at least includes a wide range of traffic congestion model, a disease diffusion model, and an air pollution and urban heat island effect model, wherein, the plurality of models are at least adapted to a traffic decision-making application, a message alert application and a disease diffusion prevention application.

11. The data processing and transmission method according to claim 9, wherein after the step of decoding the data packet to generate the second sense data, the method further comprises:

analyzing the sense information; and establishing a plurality of models which at least includes a wide range of traffic congestion model, a disease diffusion model, and an air pollution and urban heat island effect model, wherein, the plurality of models are at least adapted to a traffic decision-making application, a message alert application and a disease diffusion prevention application.

* * * * *